United States Patent
Yao

(10) Patent No.: US 6,845,514 B1
(45) Date of Patent: Jan. 25, 2005

(54) PROTECTIVE DEVICE FOR THE MEDIAN AND ULNAR NERVES

(76) Inventor: Joseph Yao, 1024 Highland Ave., Blytheville, AR (US) 72315

(*) Notice: Subject to any disclaimer, the term of this patent is extended or adjusted under 35 U.S.C. 154(b) by 0 days.

(21) Appl. No.: 10/324,297

(22) Filed: Dec. 19, 2002

(51) Int. Cl.⁷ .............................................. A41D 13/08
(52) U.S. Cl. ................. 2/16; 2/161.6; 128/878
(58) Field of Search .................. 2/16, 20, 161.1, 2/161, 163; 128/878, 879; 602/5, 21, 64

(56) References Cited

U.S. PATENT DOCUMENTS

| | | | | |
|---|---|---|---|---|
| 4,691,387 A | | 9/1987 | Lopez .......................... 2/161 A |
| 4,850,341 A | | 7/1989 | Fabry et al. ..................... 601/40 |
| 5,031,640 A | | 7/1991 | Spitzer ......................... 128/878 |
| 5,058,573 A | * | 10/1991 | Hess et al. ..................... 602/21 |
| 5,404,591 A | | 4/1995 | Brinnaand et al. ................. 2/20 |
| 5,459,883 A | * | 10/1995 | Garceau-Verbeck ......... 2/161.1 |
| 5,476,439 A | | 12/1995 | Robinson ...................... 601/40 |
| 5,634,214 A | | 6/1997 | St. Ville ....................... 2/161.2 |
| D381,132 S | * | 7/1997 | Fabry ......................... D29/123 |
| 5,810,753 A | * | 9/1998 | Eberbach ....................... 602/21 |
| 5,921,949 A | | 7/1999 | Dray ............................. 602/64 |
| 5,987,642 A | * | 11/1999 | Webster ........................... 2/19 |
| 6,006,751 A | * | 12/1999 | Spitzer ........................ 128/878 |
| 6,098,200 A | | 8/2000 | Minkow et al. ............. 2/161.1 |
| 6,200,286 B1 | | 3/2001 | Zamani ....................... 602/64 |
| 6,289,517 B1 | | 9/2001 | Minkow et al. ............. 2/161.1 |
| 6,315,748 B1 | * | 11/2001 | Morgan, Jr. .................. 602/21 |
| 6,517,501 B1 | * | 2/2003 | Slautterback .................. 602/5 |
| 2003/0125652 A1 | * | 7/2003 | Porrata et al. ................ 602/21 |
| 2003/0130604 A1 | * | 7/2003 | Porrata et al. ................ 602/21 |

* cited by examiner

*Primary Examiner*—Katherine Moran
(74) *Attorney, Agent, or Firm*—Walker, McKenzie & Walker, P.C.

(57) ABSTRACT

Protective pads placed over the palm of the hand to protect the median and ulnar nerves. The pads are placed peripheral to the nerves in order to protect them from pressure and vibration related trauma. An optional rigid splint member may be added to also protect the nerves from repetitive motion/traction irritation. Embodiments may include incorporation of the protective pads into a splint or a glove depending upon the application.

12 Claims, 4 Drawing Sheets

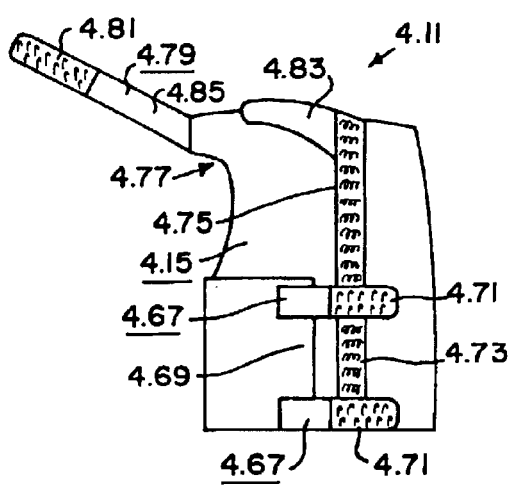
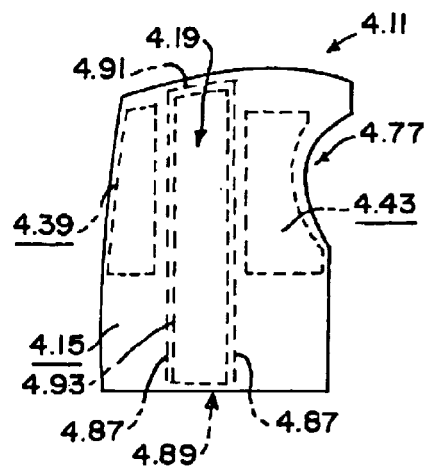
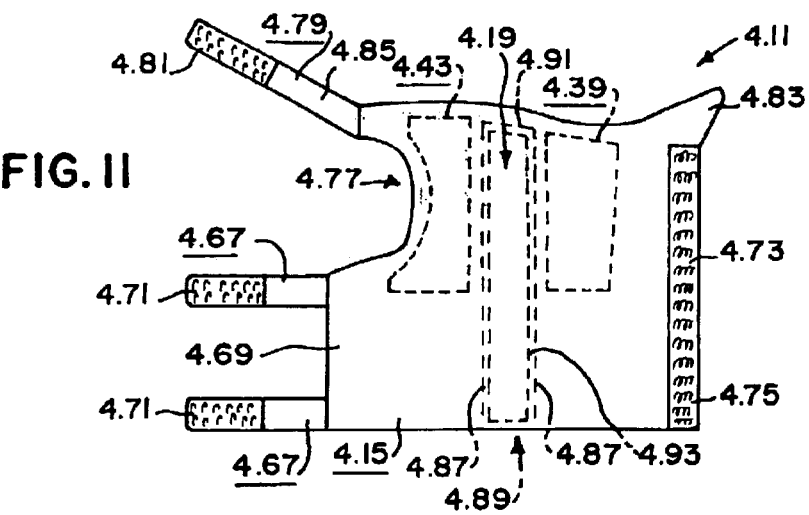
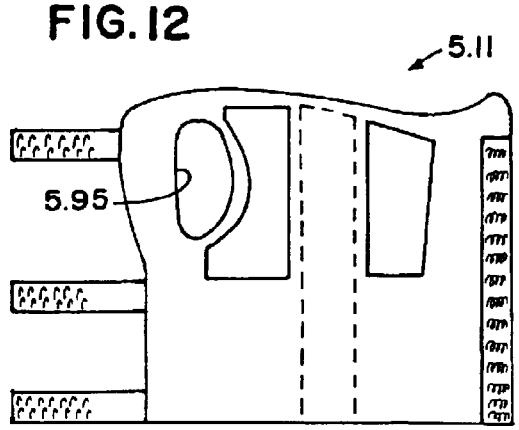
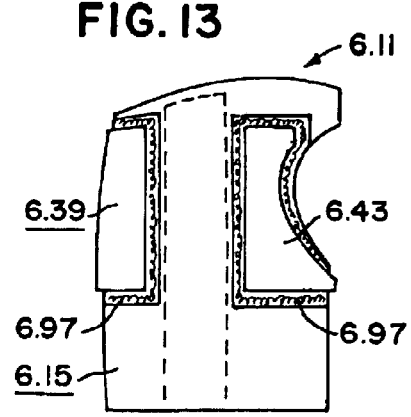

PROTECTIVE DEVICE FOR THE MEDIAN AND ULNAR NERVES

BACKGROUND OF THE INVENTION

1. Field of the Invention

The present invention relates to the use of protective pads to avoid injury to the median and ulnar nerves in the hand.

2. Information Disclosure Statement

Irritation and injury to the median (carpal tunnel syndrome) and ulnar (Guyon's canal syndrome) nerves in the hand is a common problem. The nerves pass through separate fibro-osseous canals within the wrist/palm. Nerve injury may occur as a result of compression, vibration, and traction. Common causes of nerve compression include use of a computer keyboard and mouse (mouse use places pressure primarily on the ulnar nerve), and holding a bicycle handlebar. Vibration induced nerve injury may occur from using gardening equipment (i.e., power lawn mowers, gasoline powered blowers, power string trimmers), operating heavy equipment (i.e., back hoes, road graders, tractors), and sports utilizing racquets or bats. Traction related nerve irritation might arise from frequent repetitive tasks involving hand/wrist motion such as occurs with assembly line work. Many activities may produce nerve irritation or injury through a combination of mechanisms such as compression and vibration. Examples of such activities include factory work involving the use of hand held power tools, driving/racing cars or boats, and piloting aircraft.

Nerve irritation in the hand may present with symptoms of tingling/numbness, pain, and weakness. The anatomical distribution of symptoms is dependent upon the location of nerve injury. Injury to the median nerve in the wrist/palm (i.e., carpal tunnel syndrome) typically involves sensory disturbances involving the thumb, index, long, and radial half ring fingers. Sensory disturbances associated with ulnar nerve injury in the wrist/palm (i.e., Guyon's canal syndrome) typically involve the small and ulnar half ring fingers. Motor involvement can include atrophy of the thenar muscles (i.e., median nerve injury) or hypothenar muscles (i.e., ulnar nerve) resulting in grip and pinch weakness. Pain is usually worse with activity. Night symptoms are a frequent complaint.

Treatment for median and ulnar nerve injury at the wrist/palm includes nonsteroidal anti-inflammatory medications (i.e., NSAIDs), cock-up wrist splints, activity modification, and local steroid injections into the nerve canals. Surgical decompression of the canals can be performed in those cases that do not improve with nonsurgical therapy.

Standard treatment for injury/irritation of the median and ulnar nerves at the wrist/palm includes the use of a cock-up wrist splint. These splints consist of a fabric or an elastic material body into which the hand and wrist are placed. A metal strip is incorporated into the volar aspect of the material body serving to maintain the wrist in a neutral position where nerve canal pressure is minimized. The body of the splint is generally secured with Velcro® straps allowing some degree of fit adjustment. This type of splint avoids excessive wrist dorsiflexion or palmarflexion, positions that increase nerve canal pressure and, hence, nerve irritation. Cock-up wrist splints also prevent repetitive wrist movements that can also cause nerve irritation. However, these splints do not address direct external nerve compression. In fact, the volar metal support overlies the nerves and may potentially transfer pressure to them.

Brinnand et al (U.S. Pat. No. 5,404,591 issued Apr. 11, 1995) designed a glove with padding around the wrist/carpal area to protect the skin and bones in this area. The glove was designed for users of electronic input devices such as a computer mouse or stylus. The padding was located across the entire wrist and palm without any recess to off load the median or ulnar nerves.

Dray (U.S. Pat. No. 5,921,949 issued Jul. 13, 1999) sought to protect the median nerve by designing a circumferential compression strap applied around the wrist. Compression by the strap was supposed to relax the flexor retinaculum and reverse anterior to posterior prolapse of the carpal tunnel thereby reducing stress on the median nerve. This orthosis did not address direct external pressure to the median and ulnar nerves. It also did not address traction stress to the median and ulnar nerves caused by repetitive wrist motion.

Gloves with pads have been produced to prevent vibration related nerve injury. Gloves have also been made incorporating air bladders to prevent transfer to vibration to the hand (U.S. Pat. No. 5,771,490 issued Jun. 30, 1998 to Reynolds, et al and U.S. Pat. No. 5,537,688 issued Jul. 23, 1996 to Reynolds, et al).

A variety of gloves have been developed for use in sports (U.S. Pat. No. 4,691,387 issued to Lopez on Sep. 8, 1987) such as racquetball, golf (U.S. Pat. No. 5,634,214 issued to St. Ville on Jun. 3, 1997), and baseball. These gloves are typically designed to improve a player's grip on the handle of the racquet or bat. Some of these gloves include padding in various areas. But, they do not specifically address nerve protection through impact or pressure avoidance to the nerves.

Standard bicycling gloves generally include a broad pad or combination of multiple pads to cushion the entire palm including the course of the median and ulnar nerves. Pads in standard bicycling gloves do not avoid pressure to the nerves since they lie directly over the nerves. There are at least three bicycling gloves that specifically address nerve irritation related to gripping a bicycle handlebar. The first such glove was designed by Minkow, et al (U.S. Pat. No. 6,289,517 issued Sep. 18, 2001) and it addresses protection of the median and ulnar nerves by placing padding of increased thickness directly over the nerves. The purpose of the padding is to cushion the nerves. The design of this glove does not attempt to relieve pressure from the nerves.

The second bicycling glove designed for nerve protection is the Louis Girneau Ergo Air glove (World patent pending). Information in its advertisement and packaging material states that it has "vents to prevent fatigue of the ulnar and median nerves." The advertisement states "the unique ventilation system on the inside of the palm reduces numbness by increasing moisture diffusion and reducing heat." Ventilation is afforded by stretch knit material in the palm. Other claims in the advertisement indicate "padding strategically placed to dampen vibration" and "padding eliminates pressure on the ulnar nerve." Inspection of the product drawing depicted in the advertisement and analysis of the actual glove indicates that there is a U-shaped pad attached to the palm of the glove. The portions of the pad that comprise the longitudinal limbs of the U pass directly over the median and ulnar nerves. Hence, the pads cushion the median and ulnar nerves. But, the pads do not relieve pressure from the nerves by virtue of their location over the nerves.

The Grandoe Shock Tek (Trademark registration date Jan. 6, 1998 issued to Spitzer) is the third glove designed with nerve protection in mind. This glove utilizes prior art described in U.S. Pat. No. 6,006,751 issued Dec. 28, 1999 to Spitzer. The design of this glove specifically addresses pressure relief of the median nerve by using pads (Spitzer described using interrupted resilient protection to impart greater flexibility) placed parallel to the median nerve. There is a recess between the pads located over the median nerve. The Shock Tek glove does not address pressure relief for the ulnar nerve. In fact, the ulnar pad lies over the ulnar nerve.

There have been some inventions created to protect the median nerve by avoiding pressure to the nerve. These inventions have not addressed protection of the ulnar nerve with the exception of one by Spitzer (U.S. Pat. No. 6,006,751) in which he describes one embodiment of his invention that is a glove assembly that has a secondary notch situated over the ulnar nerve to prevent compression to the ulnar nerve. Spitzer's diagram of the secondary notch shows it to be a focal, concave cutout in the ulnar base of the resilient protector that is located ulnar to the median nerve. Therefore, only the proximal portion of the ulnar nerve is off-loaded as it courses through the proximal palm.

Eberbach (U.S. Pat. No. 5,810,753 issued Sep. 22, 1998) designed a wrist brace with parallel load-bearing members separated by a space over the median nerve. These load-bearing members extended from the distal forearm to the palm. The description of the size and location of the ulnar load-bearing member potentially placed it over the ulnar nerve.

Zamani (U.S. Pat. No. 6,200,286 B1 issued Mar. 13, 2001) described a wrist splint that was essentially a modification of a standard cock-up wrist splint. Instead of a flat volar rigid support typical of the standard splint, Zamani used a rigid preformed member with raised contact portions located on the sides of the carpal tunnel to avoid pressure to the median nerve. The brace did not include any mechanism for off-loading the ulnar nerve.

Nothing in the known prior art, either singly or in combination, discloses or suggests the present invention.

BRIEF SUMMARY OF THE INVENTION

The problem of irritation/injury to the median and ulnar nerves in the wrist/palm can be addressed by using pads placed anatomically correctly peripheral to the nerves. Pads are placed ulnar to the ulnar nerve and radial to the median nerve. The objective is to avoid pressure to the nerves rather than to cushion them, so no padding is placed directly over the nerves. This type of pad configuration can avoid pressure and minimize transmission of vibration to the median and ulnar nerves. This pad configuration can be applied to a variety of different situations where protection of the median and ulnar nerves is desired. A rigid support can be added when limitation of wrist motion is desired. The features of the invention may be modified for use for various applications including but not limited to office, industrial, and sports uses.

BRIEF DESCRIPTION OF THE SEVERAL VIEWS OF THE DRAWINGS

FIG. 9 is a dorsal view of an embodiment of the protective device of the present invention designed especially for nerve protection for computer uses, with the device shown in a partially open position.

FIG. 10 is a palmar view of the protective device of FIG. 9, with the device shown in a fully closed position.

FIG. 11 is a palmar view of the protective device of FIG. 9, with the device shown in a fully open position.

FIG. 12 is a palmar view similar to FIG. 11 but showing modifications relating to a thumbhole.

FIG. 13 is a palmar view similar to FIG. 10 but showing modifications relating to adjustable pads.

DETAILED DESCRIPTION OF THE INVENTION

Figure 1:
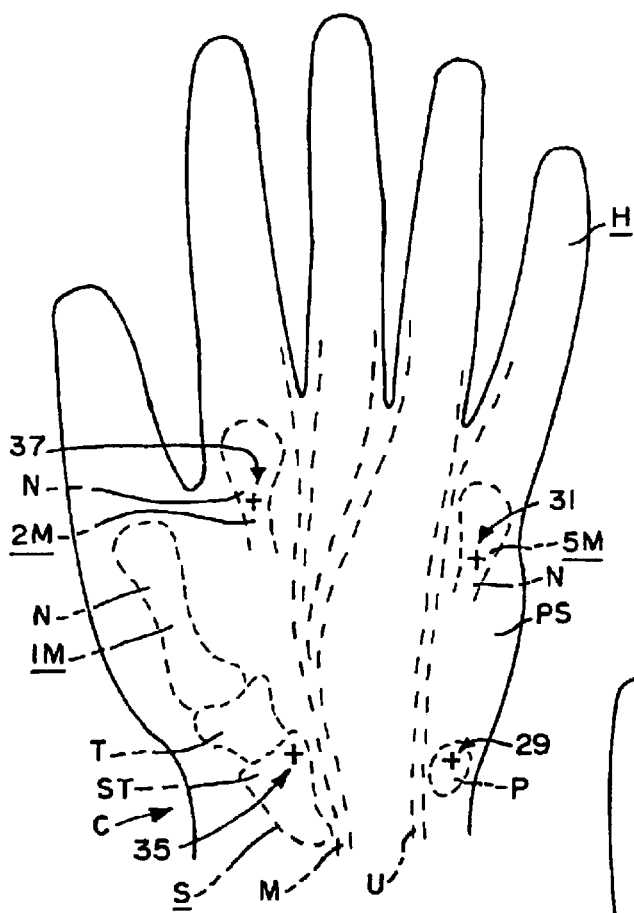
FIG. 1 is a palmar view of a wearer's left hand showing certain bone structure and portions of the wearer's median and ulnar nerves in broken lines.
Figure 2:
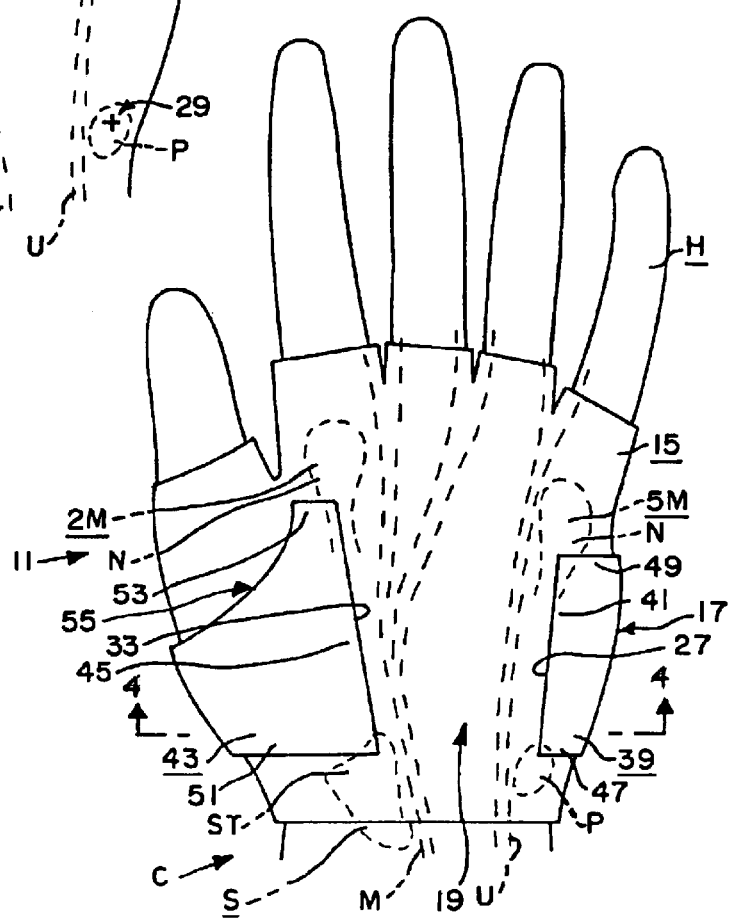
FIG. 2 is a palmar view of a wearer's left hand similar to FIG. 1 but showing a first preferred embodiment of the protective device of the present invention thereon.
Figure 3:
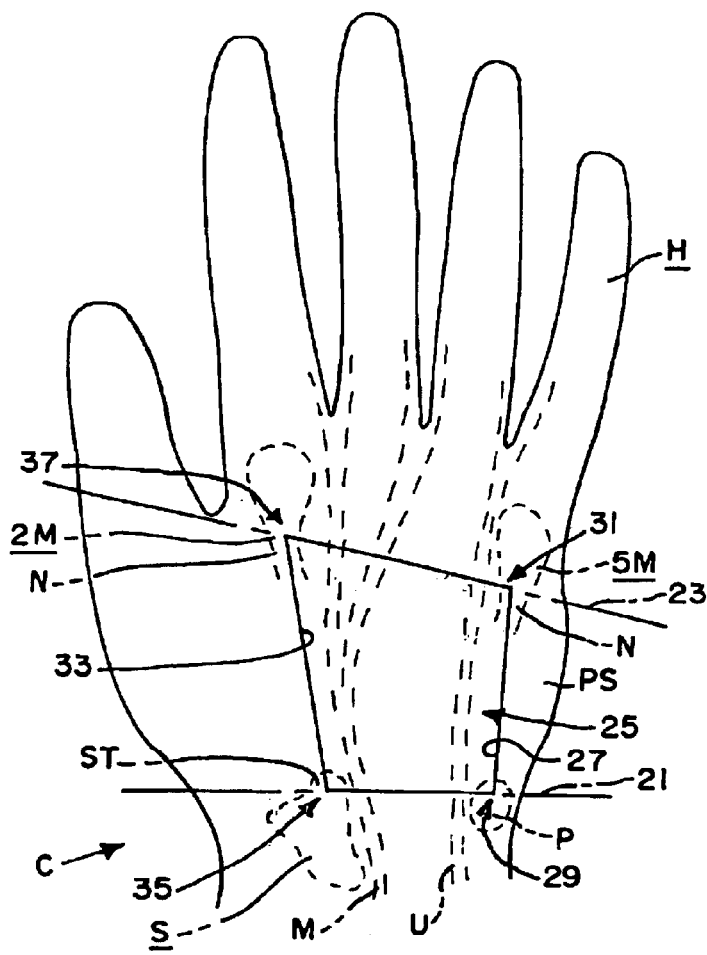
FIG. 3 is a palmar view of a wearer's left hand similar to FIG. 1 but showing diagrammatically a window created by the protective device of the present invention.
Figure 4:
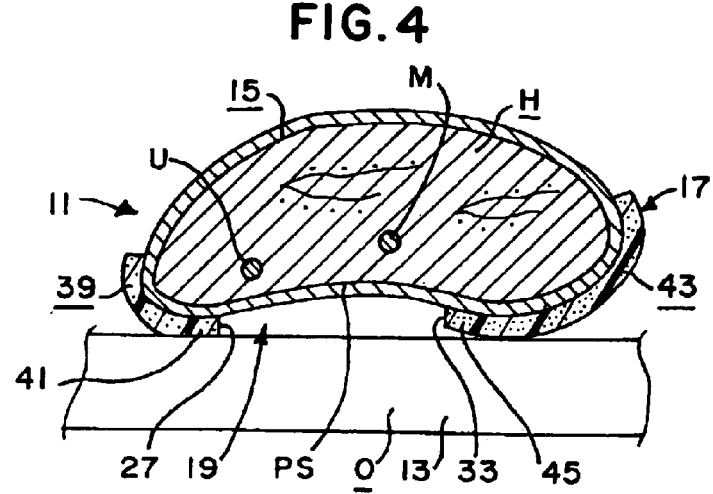
FIG. 4 is a sectional view substantially as taken on line 4—4 of FIG. 2, with the wearer's hand rotated 180°, to a palm down position, and engaging an object such as the handlebar of a bicycle.

The protective device of the present invention is for positioning between the palm or palmar side PS of a wearer's hand H and an object O, and for protecting the median nerve M and ulnar nerve U of the palmar side PS of the wearer's hand H. A somewhat diagrammatic view of the palmar side PS of a user's or wearer's hand H is shown in FIGS. 1–3, with certain bone structure (including the scaphoid S, pisiform P, distal end of the second metacarpal 2M, and distal end of the fifth metacarpal 5M) and with the courses of certain critical, somewhat superficial portions of the wearer's median nerves M and ulnar nerves U shown in broken lines. The distal end of each metacarpal 2M, 5M has a neck portion or level N.

A preferred embodiment of the protective device of the present invention is shown in FIGS. 2 and 4–6 as a glove 11 for use in cycling or the like. The glove 11 is designed to be positioned between the palm or palmar side PS of the wearer's hand H and an object O such as the handlebars 13 of a bicycle (see FIG. 4), etc., and for protecting the median nerves M and ulnar nerves U of the palm or palmar side PS of the wearer's hand H.

The glove 11 includes a body member 15 for covering at least a portion of the palmar side PS of the wearer's hand H, and pad means 17 attached to the body member 15 for providing a cushion between the palmar side PS of the wearer's hand H and the object O (i.e., the handlebars 13). A critical feature of the present invention is that the pad means 17 has an opening 19 above the median nerves M and ulnar nerve U on the palmar side PS of the wearer's hand H from a point proximally at least adjacent a generally transverse proximal plane 21 extending through the wearer's carpus C to a point distally at least adjacent a generally transverse distal plane 23 through the wearer's metacarpal necks N when the body member 15 is covering at least a portion of the palmar side PS of the wearer's hand H. The opening 19 thus forms a window 25 (shown diagrammatically in FIG. 3) above the median nerves M and ulnar nerve U of the palmar side PS of the wearer's hand H from a point proximally at least adjacent the proximal plane 21 extending through the wearer's carpus C to a point distally at least adjacent the distal plane 23 through the wearer's metacarpal necks N. The purpose and function of the opening 19 and window 25 is to protect the median nerve M and ulnar nerve U by preventing pressure from being applied to the median and ulnar nerves M, N when the object O (e.g., handlebars 13) is gripped. The opening 19, or window 25, preferably has an ulnar border 27 extending from a proximal point 29 adjacent the wearer's pisiform P to a distal point 31 adjacent the neck level N of the wearer's fifth metacarpal 5M, and a radial border 33 extending from a proximal point 35 adjacent the scaphoid tuberosity ST of the wearer's scaphoid S to a distal point 37 adjacent the neck level N of the wearer's second metacarpal 2M.

The pad means 17 preferably includes an ulnar pad 39 having a radial edge 41 forming the ulnar border 27 of the opening 19 of the pad means 17, and a radial pad 43 having an ulnar edge 45 forming the radial border 33 of the opening 19 of the pad means 17. While the ulnar and radial pads 39, 43 may be integral, they are preferably separate from one another as clearly shown in the drawings.

The ulnar pad 39 preferably has a proximal edge 47 extending along a transverse plane through the wearer's pisiform P, and a distal edge 49 extending along a transverse plane through the neck N of the wearer's fifth metacarpal 5M. The ulnar extent of the ulnar pad 39 is preferably at the volar ulnar border of the hand H. Such boundaries may define the ulnar pad 39 as being substantially trapezoidal in shape. The distal edge 49 of the ulnar pad 39 may be slightly longer, or wider, than the proximal edge 47 thereof.

The radial pad 43 preferably has a proximal edge 51 extending along a transverse plane through the wearer's scaphoid tuberosity ST, and a distal edge 53 extending along a transverse plane through the neck N of the wearer's second metacarpal 2M. The radial pad 43 may be substantially rectangular in shape with a concave cutout 55 distal radially to accommodate the base of the wearer's thumb.

The basic feature of the protective pads 39, 43 is demonstrated. The radial pad 43 is placed radial to the median nerve M, and the ulnar pad 39 is placed ulnar to the ulnar nerve U. The opening 19, or window 25, is present between the ulnar and radial pads 39, 43 so there is no padding located over either the median or ulnar nerves M, U.

Figure 5:
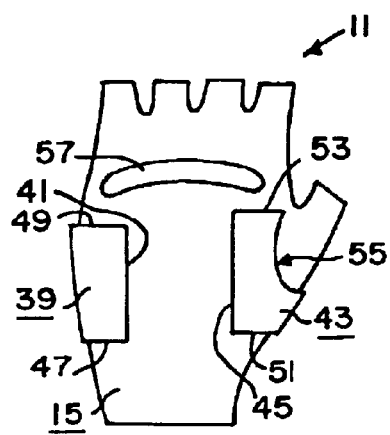
FIG. 5 is a palmar view of an embodiment of a somewhat modified version of first preferred embodiment protective device of the present invention designed especially for nerve protection for bicycling uses, with the device shown in a closed position and for a wearer's right hand.

FIG. 5 is a palmar view of the embodiment of the protective device of the invention for use in a bicycling glove 11. This type of glove 11 can also be modified for use with activities including but not limited to driving, operating heavy equipment, operating power gardening equipment, weight lifting, and factory work. The standard bicycling glove 11 extends from the wrist proximally to just proximal to the proximal interphalangeal joints of the fingers and the interphalangeal joint of the thumb distally. The body or body member 15 of the glove 11 can be made of mesh material or a moisture-wicking material such as Cool Max® on the dorsum and a more durable material such as leather or leatherette on the palmar side. Additional layer(s) of leather or leatherette material are placed in the thumb-index web space to enhance wear properties of the glove 11. The materials used for the body 15 of the glove can be of varying colors and patterns to enhance the visual appearance of the glove 11 and to suit personal preference. The ulnar and radial nerve protection pads 39, 43 may be sewn into the palmar aspect of the body 15 of the glove 11 between a thinner layer of material inside the glove and the thicker, more durable leatherette outer material. The anatomical location of the ulnar and radial pads 39, 43 is critical to the optimum function and performance of the present invention. The ulnar extent of the ulnar pad is at the volar ulnar border of the hand and does not, preferably, wrap around the ulnar border of the hand. The opening 19, or window 25, between the ulnar and radial pads 39, 43 is especially designed to prevent pressure to the median and ulnar nerves M, U.

As shown in FIG. 5, a thinner, slightly curved, distal transverse pad 57 may be also attached (e.g., sewn) to the palmar aspect of the body 15 of the glove 11 over the area of the $2^{nd}$ through $5^{th}$ metacarpal heads 2M, 5M to provide cushioning. Most of the pressure from gripping a bicycle handlebar 13 is transferred through the proximal palm, so the ulnar and radial pads 39, 43 should preferably to be thicker than the distal transverse pad 57. The ulnar and radial pads 39, 43 can be of equal thickness unlike a computer use splint where the radial pad is slightly thicker as will be hereinafter explained.

Figure 6:
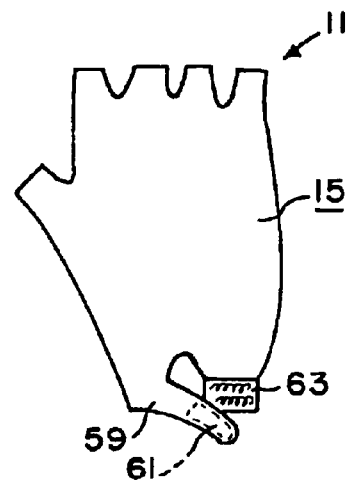
FIG. 6 is a dorsal view of the device of FIG. 5, with the device shown in a partially open position.

FIG. 6 is a dorsal view of the bicycling glove 11. A strap 59 may be present at the proximal portion of the glove 11 arising from the radial side of the body 15 of the glove 11. Velcro® loop material 61, or the like, may be attached to the undersurface of this strap 59. Velcro® hook material 63 or the like may be attached to the proximal surface of the ulnar portion of the glove body 15 to coact with the Velcro® loop material 61 and create a means by which the strap 59 can be adjustably secured to the body 15 of the glove 11.

Figure 7:
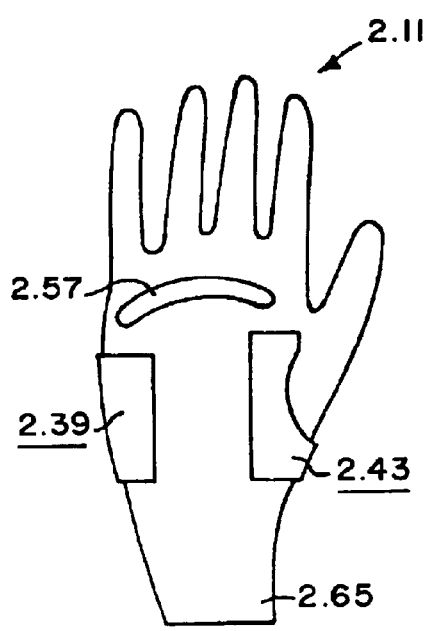
FIG. 7 is a palmar view of an embodiment of the protective device of the present invention designed especially for nerve protection for bicycling uses, with the device shown in a closed position and with full finger protection.

FIG. 7 is a palmar view of a modified glove 2.11 providing full finger coverage. Applications for this type of glove 2.11 include winter bicycling and off-road/dirt bicycling and motorcycle riding. This glove 2.11 can include insulating, heat retaining materials such as Thinsulate®. This glove 2.11 may also include an extension 2.65 proximial to the wearer's wrist to aid with heat retention. This glove 2.11 also includes ulnar and radial pads 2.39, 2.43 and, preferably, a distal transverse pad 2.57 for reasons disclosed hereinabove relative to the glove 11. The location of the ulnar and radial pads 2.39, 2.43 as well as the distal transverse pad 2.57 is the same as for the glove 11. The glove 2.11 can also be used for activities such as snowmobiling and operating heavy machinery in cold environments. Off-road/dirt bicycling and motorcycle riding gloves can be made of the same or more durable materials as the partial-finger coverage glove 11. The off-road/dirt bicycling gloves can also be used for activities, such as operating power garden equipment and factory work. Materials can be used that resist abrasion, laceration, and puncture.

Figure 8:
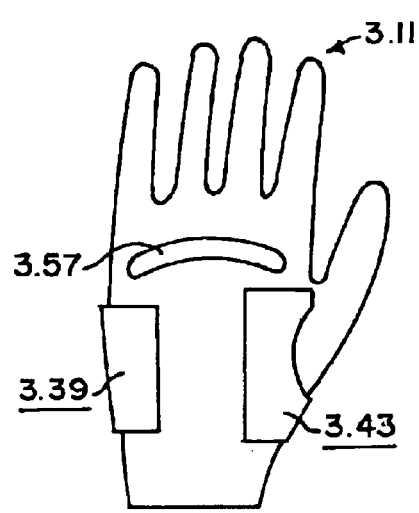
FIG. 8 is a palmar view of an embodiment of the protective device of the present invention designed especially for nerve protection for sports involving racquets or bats, etc., with the device shown in a closed position and with full finger protection.

FIG. 8 is a palmar view depicting a modified glove 3.11 providing full finger coverage for use in sports involving clubs, racquets, and bats. Examples of these sports include but are not limited to golf, tennis, badminton, racquetball, squash, and baseball. This glove may be constructed using thin, unlined leather or leatherette to optimize non-slip gripping of racquets and bats while minimizing glove thickness and maximizing tactile feedback. Ulnar and radial pads 3.39, 3.43 may be attached to the palmar aspect of the body 3.15 of the glove 3.11 by thin pieces of overlying leather or the like sewn to the glove body 3.15. A transverse pad 3.57 is sewn to the glove body 3.15 over the $2^{nd}$ through $5^{th}$ metacarpal heads. Alternatively, the pads 3.39, 3.43, 3.57 may be attached by adhesive to the glove body 3.15. A layer of leather or leatherette could cover the pads if greater durability is desired. The locations of the pads are the same as described hereinabove for the glove 11. The primary difference between this glove 3.11 and the gloves 11, 2.11 is that all of the pads are made thinner in this glove 3.11 in order to minimize bulk and to maximize tactile feedback. A dorsal proximal strap with attached Velcro® (similar to that described in FIG. 6) is used to facilitate insertion and removal of the hand from the glove 3.11 and to secure the glove 3.11 in place once the hand is inside. A partial finger coverage version of this glove 3.11 can be used for activities such as shooting firearms and for driving (for those that desire a thin glove), etc.

Another preferred embodiment of the protective device of the present invention is shown in FIGS. 9–11 as a splint 4.11 for protection of the median and ulnar nerves M, U during use of computer keyboards and computer mouses, etc. Such a splint 4.11 could also be used for factory work. The reversible feature of the splint 4.11 allows it to be used for either the right or left hands.

FIG. 9 shows the dorsal side of the splint 4.11. The splint 4.11 has a body 4.15 preferably made of two layers of elastic material in order to facilitate incorporation of design features enabling the splint to be universal. It is also possible to construct the splint in a non-reversible form. Alternative materials may be used depending upon the application. For example, a more durable material can be used for industrial applications. There may be instances where it may be advantageous to use laceration and puncture resistant materials. The material used for the splint body 4.15 can be of different colors and patterns to enhance the visual appeal of the splint. The splint body 4.15 extends from proximal to the wrist to the mid-palm in order to support the wrist while allowing unobstructed finger motion.

Multiple nonelastic straps 4.67 may be attached to the radial edge 4.69 of the splint body 4.15. Velcro® hook material 4.71 or the like may be attached to both sides of the straps 4.67 and Velcro® loop material 4.73 or the like may be attached to both sides of the ulnar border 4.75 of the splint body 4.15 in order to allow the straps 4.67 to be secured to the ulnar border 4.75 of the splint body 4.15 and avoid placing the rough Velcro® hook material 4.71 against the skin. The distal radial portion of the splint body 4.15 preferably has a concave area 4.77 to accommodate the base of the wearer's thumb.

A smooth, nonelastic strap 4.79 may be attached to the radial distal palmar portion of the splint body 4.15. This strap 4.79 has smooth edges and is designed to be pulled dorsally through the web space between the wearer's thumb and index fingers. This strap 4.79 preferably has Velcro® hook material 4.81 or the like attached to both sides of it so it can be secured to the Velcro® loop material 4.73 on the ulnar border 4.75 of the splint body 4.15. The distal ulnar portion of the splint body 4.15 preferably has an ulnar projection 4.83 that extends into the thumb-index web space to protect the skin from the Velcro® hook material 4.81 on the radial distal palmar strap 4.79. No Velcro® hook material or the like is attached to the proximal portion 4.85 of the strap 4.79 in the area where the strap 4.79 passes through the thumb-index web space in order to avoid skin irritation.

FIG. 11 is a palmar view of the splint 4.11. The radial distal palmar strap 4.79 is demonstrated in a closed or attached position. Two parallel lines of stitching 4.87 are placed in the central palmar portion of the splint body 4.15 joining the two layers of elastic splint body fabric creating a longitudinal pouch 4.89 extending from the proximal to distal aspect of splint body 4.15. The distal portion of the pouch is sewn shut transversely by a line of stitching 4.91. A substantially rigid, dinner fork-shaped, contoured aluminum metal splint member 4.93 may be attached to the body 4.15 by being slipped into the proximal portion of the splint body pouch 4.89 and pushed distally. The splint member 4.93 may be fabricated from other materials including plastic. However, aluminum has the advantage of being malleable so it can be easily contoured for a custom fit. The splint member 4.93 is unable to migrate distally out of the splint body since the distal portion of the pouch has been sewn shut by the line of stitching 4.91. The splint member 4.93 may be removed, rotated 180 degrees (palmar to dorsal), and reinserted into the pouch when switching the splint 4.11 from right to left-hand configuration, and vice versa. The splint 4.11 may be used with or without the splint member 4.93 inside of it depending upon the individual's preference.

The double layer of material used to construct the splint body 4.15 allows easy creation of the splint pouch 4.89. It also allows easy fixation of the ulnar and radial nerve protection pads 4.39, 4.43 between the two layers of material. The splint 4.11 is truly reversible since the protective pads 4.39, 4.43 are preferably located between the two layers of material and would be in the same relative locations whether the splint 4.11 is used for a right or left hand. The splint would not be truly reversible if the protective pads 4.39, 4.43 were attached to the external surface of the splint body 4.15 since the pads 4.39, 4.43 would be on the outside of the body 4.15 of the splint 4.11 when worn on one hand, and, conversely, the pads 4.39, 4.43 would be on the inside of the body 4.15 of the splint 4.11 when worn on the opposite hand.

The pads 4.39, 4.43 are preferably fabricated from a non-flowing, resilient gel material in the preferred embodiment. However, the pads 4.39, 4.43 can be made of alternative materials including but not limited to felt or foam. Sealed air bladders may also be utilized. The air bladders can be fitted with valves to permit insertion of varying volumes of air to allow adjustment of the degree of cushioning. The pads 4.39, 4.43 are preferably secured between the two layers of splint body material by circumferential stitching around the pads. The ulnar pad 4.39 is preferably trapezoidal in shape and extends proximally from the pisiform P to the neck level N of the fifth metacarpal 5M distally. The pisiform P also forms the radial border of the ulnar pad 4.39. The ulnar pad 4.39 preferably extends around the ulnar border of the wearer's hand H in order to provide cushioning to that portion of the hand H when operating a computer mouse. The distal portion of the ulnar pad 4.39 is preferably slightly wider than the proximal portion.

The radial pad 4.43 may be rectangular in shape with a concave cutout distal radially to accommodate the base of the thumb. The radial pad 4.43 extends proximally from the scaphoid tuberosity ST to the neck level N of the second metacarpal 2M distally. The scaphoid tuberosity ST forms the ulnar border of the radial pad 4.43. The trapezium T forms the radial border of the radial pad 4.43 proximally. The neck N of the first or thumb metacarpal 1M forms the radial border of the radial pad 4.43 distally. The space or opening 4.19 between the radial border of the ulnar pad 4.39 and the ulnar border of the radial pad 4.43 is left open with no padding. The carpal tunnel (median nerve M) and Guyon's canal (ulnar nerve U) are located in this space 4.19 between the ulnar and radial pads 4.39, 4.43. It is important that the ulnar and radial pads 4.39, 4.43 do not extend distal above the level of the metacarpal necks N in order to avoid interfering with finger flexion.

The radial pad 4.43 is preferably made slightly thicker than the ulnar pad 4.39 since the forearms are held in approximately 60 degrees of pronation while using a computer mouse. This position places the radial portion of the hand further away from the desktop than the ulnar portion of the hand and is responsible for greater pressure applied to the ulnar side of the hand. The slightly thicker radial pad 4.43 helps to distribute some pressure to the radial side of the hand.

FIG. 11 is a dorsal view of the splint 4.11 opened up. Features of the splint demonstrated in FIGS. 9 and 10 are again seen.

A non-reversible embodiment of the splint may also be fabricated. A single layer of material can used for the splint body of such a non-reversible splint. A partial second layer of material is used on the palmar side of the splint to secure the pads in place and create a pouch for the rigid support. Velcro® material needs to be attached only to one side of the straps and splint body in the non-reversible embodiment.

A modified splint is shown in FIGS. 12 and 13, and identified by the numeral 5.11. FIG. 12 depicts the splint 5.11 folded out and opened. FIG. 13 depicts the splint 5.11 closed. The splint 5.11 is substantially similar to the splint 4.11 but rather than a strap 4.79, the splint 5.11 has a hole 5.95 formed in the radial distal splint body 5.15 to accommodate the wearer's thumb. The hole 5.95 in the splint body 5.15 serves as a simple substitute for the web space strap 4.79 of the splint 4.11. The other features of the splint 5.11 are the same as described hereinbefore relative to the splint 4.11.

FIG. 13 is a palmar view of another variation of the splint 4.11. The splint 4.11 discloses the ulnar and radial pads 4.39, 4.43 sewn into place between the two layers of splint body fabric. The splint 6.11 shown in FIG. 13 is designed to allow variable positioning of the ulnar and radial pads 6.39, 6.43. For example, Velcro® loop material 6.97 may be attached to both sides (to allow the splint to be reversible and to prevent skin irritation) of the splint body 6.15 on its ulnar and radial sides. Velcro® hook material (not shown) may be adjustably and removably attached to the backside of the ulnar and radial pads 6.39, 6.43 so the ulnar and radial pads 6.39, 6.43 can be secured to the splint body 6.15 via the co-operation of the Velcro® loop material 6.97 on the radial and ulnar aspects of the splint body 6.15 and the Velcro® hook material on the backside of the ulnar and radial pads 6.39, 6.43. Each splint 6.11 may be provided with a right and left set of radial and ulnar pads. Alternatively, one set of radial and ulnar pads without attached Velcro® could be provided with the splint. Separate pieces of Velcro® hook material with adhesive backing could also be provided with the splint. The adhesive backing would allow the Velcro® hook material to be adhered to the side of the pads appropriate for use with a right or left hand. The pads could be trimmed with a knife or scissors for a custom fit. The Velcro® system of pad attachment allows the locations of the pads to be altered to the individual's preference.

Outline of Distinguishing Features of Various Embodiments

The following outline list certain distinguishing features for various applications of the present invention for a clearer understanding of the scope thereof:

I. General features
  A. Radial and ulnar palmar pads placed peripheral to the median and ulnar nerves to avoid pressure and transfer of vibration to the nerves.

II. Specific features
  A. Computer use
    1. Removable volar rigid support.
    2. Splint can be made to be reversible so it can be used for right or left hand.
    3. Material for the splint body can be of different colors and patterns to enhance visual appeal.
    4. The radial pad is slightly thicker than the ulnar pad to account for the hand position while using a computer mouse.
    5. Velcro® can be used in one embodiment to attach the pads to the splint body to allow the pad locations to be altered to suit individual preference.
    6. The pads can be trimmed to allow customization of their shape and size.
    7. The ulnar pad extends around the ulnar border of the hand in order to provide cushioning to that part of the hand when operating a computer mouse.
    8. The radial and ulnar pads do not extend distally beyond the level of the $2^{nd}$ through $5^{th}$ metacarpal necks in order to avoid interference with finger flexion.
  B. Bicycling glove
    1. Additional thinner, slightly curved, transverse pad distally to cushion the $2^{nd}$ through $5^{th}$ metacarpal heads.
    2. The ulnar pad does not wrap around the ulnar border of the hand.
    3. The radial and ulnar pads are equal in thickness.
    4. The body of the glove can be made of mesh material or a moisture wicking material on the dorsum and a more durable material on the palmar side.
    5. The materials used for the body of the glove can be of varying colors and patterns to enhance the visual appearance of the glove.
    6. Partial finger coverage and full finger coverage embodiments.
    7. Cold weather gloves can include insulating, heat retaining materials. These gloves also extend proximal to the wrist to aid with heat retention.
    8. Off-road/dirt bicycling and motorcycle riding gloves can be made of more durable materials.
  C. Glove for driving/racing cars or boats, piloting aircraft
    1. Pad configuration similar to bicycling glove.
    2. The glove body of standard driving and piloting gloves can be made of thin, non-slip material for comfort and enhanced tactile feedback. The material can be perforated to prevent heat buildup.
    3. Racing gloves can provide full finger coverage and include fire retardant material.
  D. Glove for operating heavy equipment, power gardening equipment, industrial use
    1. Pad configuration similar to bicycling glove, but the distal transverse pad is thicker to provide more vibration protection.
    2. Durable material that is resistant to abrasion and soiling.
    3. Depending upon the application, material may be utilized that is laceration and perforation resistant.

E. Glove for sports involving clubs, racquets, and bats
   1. Generally full finger coverage glove.
   2. Partial finger coverage embodiment may be used for shooting firearms.
   3. Pad configuration similar to bicycling glove, but all pads are thinner in order to minimize interference with grip and tactile feedback.
   4. Glove body material is thinner than bicycling and industrial gloves in order to minimize bulk and interference with grip and tactile feedback.
F. Glove for weight lifting
   1. Pad configuration similar to bicycling glove, but the distal transverse pad is thicker to provide more cushioning.
   2. Partial finger coverage glove body.
G. Glove for factory assembly line work
   1. Pad configuration similar to bicycling glove.
   2. Optional removable volar rigid splint so repetitive motion stresses to the median and ulnar nerves can be avoided.
   3. Partial or full finger coverage embodiments depending upon the application.
   4. Heavier or lighter glove body materials depending upon the application and how much dexterity is required.

Although the present invention has been described and illustrated with respect to preferred embodiments and preferred uses therefor, it is not to be so limited since modifications and changes can be made therein which are within the full intended scope of the invention. The various embodiments of the invention described herein exemplify its use in some common applications. The description herein is not intended to be exhaustive or all-inclusive. The invention may be used in other situations and applications where the objective is to protect the median and/or ulnar nerves.

What is claimed is:

1. A protective device for positioning between the palm of a wearer's hand and an object, and for protecting the median and ulnar nerves of the palm of the wearer's hand; said protective device comprising:
   (a) a body member for covering at least a portion of the palm of the wearer's hand;
   (b) pad means attached to said body member for providing a cushion between the palm of the wearer's hand and the object; said pad means having an opening above the median and ulnar nerves of the palm of the wearer's hand from a point proximally at least adjacent a transverse plane extending through the wearer's carpus to a point distally at least adjacent a transverse plane through the wearer's metacarpal necks when said body member is covering at least a portion of the palm of the wearer's hand; said opening having an ulnar border and an radial border; said pad means having sufficient thickness at said ulnar and radial borders of said opening for spacing the object away from the palm of the wearer's hand along the median and ulnar nerves of the palm of the wearer's hand and for avoiding transmission of vibration and pressure to the median and ulnar nerves of the palm of the wearer's hand from the object.

2. The protective device of claim 1 in which said ulnar border extends from a proximal point adjacent the wearer's pisiform to a distal point adjacent the wearer's fifth metacarpal neck level; and in which said radial border extends from a proximal point adjacent the wearer's scaphoid tuberosity to a distal point adjacent the wearer's second metacarpal neck level.

3. The protective device of claim 1 in which said body member forms the body of a glove for being worn by the wearer.

4. The protective device of claim 1 in which said body member forms the body of a splint.

5. The protective device of claim 4 in which is included a substantially rigid splint member attached to said body member.

6. A protective device for positioning between the palm of a wearer's hand and an object, and for protecting the median and ulnar nerves of the palm of the wearer's hand; said protective device comprising:
   (a) a body member for covering at least a portion of the palm of the wearer's hand;
   (b) pad means attached to said body member for providing a cushion between the palm of the wearer's hand and the object; said pad means having an opening above the median and ulnar nerves of the palm of the wearer's hand from a point proximally at least adjacent a transverse plane extending through the wearer's carpus to a point distally at least adjacent a transverse plane through the wearer's metacarpal necks when said body member is covering at least a portion of the palm of the wearer's hand; said opening of said pad means having an ulnar border extending from a proximal point adjacent the wearer's pisiform to a distal point adjacent the wearer's fifth metacarpal neck level, and having a radial border extending from a proximal point adjacent the wearer's scaphoid tuberosity to a distal point adjacent the wearer's second metacarpal neck level; said pad means including an ulnar pad having a radial edge forming the ulnar border of said opening of said pad means, having a proximal edge extending along a transverse plane through the wearer's pisiform, and having a distal edge extending along a transverse plane through the wearer's fifth metacarpal neck level; said pad means having sufficient thickness at said ulnar and radial borders of said opening for spacing the object away from the palm of the wearer's hand along the median and ulnar nerves of the palm of the wearer's hand and for avoiding transmission of vibration and pressure to the median and ulnar nerves of the palm of the wearer's hand from the object.

7. The protective device of claim 6, in which said ulnar pad extends around the ulnar border of the wearer's hand.

8. A protective device for positioning between the palm of a wearer's hand and an object, and for protecting the median and ulnar nerves of the palm of the wearer's hand; said protective device comprising:
   (a) a body member for covering at least a portion of the palm of the wearer's hand;
   (b) pad means attached to said body member for providing a cushion between the palm of the wearer's hand and the object; said pad means having an opening above the median and ulnar nerves of the palm of the wearer's hand from a point proximally at least adjacent a transverse plane extending through the wearer's carpus to a point distally at least adjacent a transverse plane through the wearer's metacarpal necks when said body member is covering at least a portion of the palm of the wearer's hand; said opening of said pad means having an ulnar border extending from a proximal point adjacent the wearer's pisiform to a distal point adjacent the wearer's fifth metacarpal neck level, and having a radial border extending from a proximal point adjacent the wearer's scaphoid tuberosity to a distal point adjacent the wearer's second metacarpal neck level; said pad means including an ulnar pad having a radial edge forming the ulnar border of said opening of said pad means, having a proximal edge extending along a transverse plane through the wearer's pisiform, and having a distal edge extending along a transverse plane through the wearer's fifth metacarpal neck level; said ulnar pad extending around the ulnar border of the wearer's hand; said ulnar pad being trapezoidal in shape.

9. The protective device of claim 8 in which said distal edge of said ulnar pad is slightly wider than said proximal edge thereof.

10. A protective device for positioning between the palm of a wearer's hand and an object, and for protecting the median and ulnar nerves of the palm of the wearer's hand; said protective device comprising:

(a) a body member for covering at least a portion of the palm of the wearer's hand;

(b) pad means attached to said body member for providing a cushion between the palm of the wearer's hand and the object; said pad means having an opening above the median and ulnar nerves of the palm of the wearer's hand from a point proximally at least adjacent a transverse plane extending through the wearer's carpus to a point distally at least adjacent a transverse plane through the wearer's metacarpal necks when said body member is covering at least a portion of the palm of the wearer's hand; said opening of said pad means having an ulnar border extending from a proximal point adjacent the wearer's pisiform to a distal point adjacent the wearer's fifth metacarpal neck level, and having a radial border extending from a proximal point adjacent the wearer's scaphoid tuberosity to a distal point adjacent the wearer's second metacarpal neck level; said pad means including a radial pad having an ulnar edge forming the radial border of said opening of said pad means, having a proximal edge extending along a transverse plane through the wearer's scaphoid tuberosity, and having a distal edge extending along a transverse plane through the wearer's second metacarpal neck level; said pad means having sufficient thickness at said ulnar and radial borders of said opening for spacing the object away from the palm of the wearer's hand along the median and ulnar nerves of the palm of the wearer's hand and for avoiding transmission of vibration and pressure to the median and ulnar nerves of the palm of the wearer's hand from the object.

11. A protective device for positioning between the palm of a wearer's hand and an object, and for protecting the median and ulnar nerves of the palm of the wearer's hand; said protective device comprising:

(a) a body member for covering at least a portion of the palm of the wearer's hand;

(b) pad means attached to said body member for providing a cushion between the palm of the wearer's hand and the object; said pad means having an opening above the median and ulnar nerves of the palm of the wearer's hand from a point proximally at least adjacent a transverse plane extending through the wearer's carpus to a point distally at least adjacent a transverse plane through the wearer's metacarpal necks when said body member is covering at least a portion of the palm of the wearer's hand; said opening of said pad means having an ulnar border extending from a proximal point adjacent the wearer's pisiform to a distal point adjacent the wearer's fifth metacarpal neck level, and having a radial border extending from a proximal point adjacent the wearer's scaphoid tuberosity to a distal point adjacent the wearer's second metacarpal neck level; said pad means including a radial pad having an ulnar edge forming the radial border of said opening of said pad means, having a proximal edge extending along a transverse plane through the wearer's scaphoid tuberosity, and having a distal edge extending along a transverse plane through the wearer's second metacarpal neck level; said radial pad being rectangular in shape with a concave cutout distal radially to accommodate the base of the wearer's thumb.

12. A protective device for positioning between the palm of a wearer's hand and an object, and for protecting the median and ulnar nerves of the palm of the wearer's hand; said protective device comprising:

(a) a body member for covering at least a portion of the palm of the wearer's hand;

(b) pad means attached to said body member for providing a cushion between the palm of the wearer's hand and the object; said pad means having an opening above the median and ulnar nerves of the palm of the wearer's hand from a point proximally at least adjacent a transverse plane extending through the wearer's carpus to a point distally at least adjacent a transverse plane through the wearer's metacarpal necks when said body member is covering at least a portion of the palm of the wearer's hand; said opening of said pad means having an ulnar border extending from a proximal point adjacent the wearer's pisiform to a distal point adjacent the wearer's fifth metacarpal neck level, and having a radial border extending from a proximal point adjacent the wearer's scaphoid tuberosity to a distal point adjacent the wearer's second metacarpal neck level; said pad means including a radial pad having an ulnar edge forming the radial border of said opening of said pad means, having a proximal edge extending along a transverse plane through the wearer's scaphoid tuberosity, and having a distal edge extending along a transverse plane through the wearer's second metacarpal neck level; said radial pad being thicker than said ulnar pad.

* * * * *